United States Patent [19]
Hautea et al.

[11] Patent Number: 5,460,783
[45] Date of Patent: Oct. 24, 1995

[54] APPARATUS FOR AUTOMATICALLY REMOVING MICROTITER WELL-STRIPS FROM WELL-STRIP HOLDERS

[75] Inventors: Nelson S. Hautea; Kenneth L. Aeschbacher; William B. Freese, all of San Diego, Calif.

[73] Assignee: Synbiotics Corporation, San Diego, Calif.

[21] Appl. No.: 260,468

[22] Filed: Jun. 14, 1994

[51] Int. Cl.⁶ .................................... G01N 37/00
[52] U.S. Cl. ................ 422/104; 422/63; 422/65; 422/99; 435/809; 435/287.3; 436/43; 436/47; 436/809
[58] Field of Search ................ 422/63, 65, 99, 422/100, 104; 435/300, 301, 809; 436/43, 45, 183.47, 809; 206/531; 425/444; 249/69, 60

[56] References Cited

U.S. PATENT DOCUMENTS

| | | | |
|---|---|---|---|
| 3,649,464 | 3/1972 | Freeman | 422/99 |
| 4,154,795 | 5/1979 | Thorne | 422/99 |
| 4,571,087 | 2/1986 | Ranney | 366/108 |
| 4,919,894 | 4/1990 | Daniel | 422/104 |
| 4,948,442 | 8/1990 | Manns | 156/73.1 |
| 5,055,271 | 10/1991 | Golias et al. | 422/99 |
| 5,096,672 | 3/1992 | Tervamäki et al. | 422/102 |
| 5,213,766 | 5/1993 | Flesher et al. | 422/102 |
| 5,284,623 | 2/1994 | Yamori et al. | 422/99 |
| 5,290,521 | 3/1994 | De Stefano, Jr. | 422/99 |

*Primary Examiner*—James C. Housel
*Assistant Examiner*—Long V. Le
*Attorney, Agent, or Firm*—Edward S. Irons

[57] ABSTRACT

An apparatus for automatically removing well-strips from well-strip holders. The apparatus includes a frame and a base plate for receiving a plurality of well-strip holders, each holder having a plurality of well-receiving areas and corresponding apertures with the individual wells of the well-strips positioned in the areas so as to overlie the apertures. A pneumatically-operated movable drive member is attached to the frame so as to be movable in a substantially vertical direction toward and away from the base plate and well-strip holders. The movable member has a plurality of well-strip engaging portions secured to the underside thereof, each portion including a plurality of pegs that pass into the open end of the apertures formed in the well-strip holders to contact the well-strips and remove same from the holders.

19 Claims, 4 Drawing Sheets

5,460,783

APPARATUS FOR AUTOMATICALLY REMOVING MICROTITER WELL-STRIPS FROM WELL-STRIP HOLDERS

BACKGROUND OF THE INVENTION

1. Field of the Invention

The present invention relates to the production of microtiter well-strips and, more particularly, to the removal of microtiter well-strips from holders which support the well-strips during the various processing steps to which the well-strips are subjected.

2. Description of Relevant Art

The use of microtiter well-strips including individual wells, recesses, cups, etc. for receiving samples of fluid to be tested, e.g, body fluids, is well known. Such well-strips may be in the form of a sheet of plastic with a plurality of wells formed therein by molding, drilling, or any other suitable process. The particular configuration and size of the well-strips may vary. For example, several well-strips may be joined together to form a square or rectangular grid of wells.

The individual wells of the well strips are used to contain fluid samples for various test procedures, e.g., isotopic or non-isotopic immuno assays. It often is necessary or desirable to pre-treat the individual wells or cups prior to placement of the fluid to be tested therein. For example, the wells may be treated with a wetting agent for growing cell cultures, or with an antigen or antibody coating for enzyme linked immuno-sorbent assays to determine the antibody or antigen content of the fluid. It will be recognized, of course, that these are only a few of the uses for microtiter well-strips.

It is necessary to support the well-strips as they undergo various processing or pretreating steps such as those mentioned above. A typical support for the well-strips is a holder in the form of a plate or tray having a plurality of recesses or depressions configured to receive the individual wells of the well-strips. The well-strip holder supports the well-strips, the latter usually being manufactured of a relatively inexpensive material and having a relatively minimal size. The well-strip holder, on the other hand, typically is manufactured of a sturdy material and/or has a substantial thickness as compared with the well-strips so as to enable its reuse. The holder receives and supports the well-strips and provides a strong base for handling same by various equipment during the processing steps. However, it is necessary to remove the well-strips from the holders when the processing or manufacturing thereof is complete.

It is known in the art to form the well-holders with apertures extending therethrough which receive the individual wells or cups of the well-strips. The individual wells or cups may be manually removed from the holders by pushing them out through the apertures. See U.S. Pat. No. 4,154,795.

It also is known in the art to manually remove the well-strips from the well-strip holders by using a wooden block having pegs. The pegs engage some or all of the individual wells through the apertures in the holders to pop-out the well-strips. However, several problems are inherent in such removal methods. For example, manual removal of the well-strips is time consuming and requires precise alignment between the pegs and well-holder apertures in order to prevent damage to the well-holders. Accordingly, there is a need in the art for an apparatus for removing well-strips from well-strip holders that is free of the problems present in prior art apparatus.

SUMMARY OF THE INVENTION

The present invention provides an apparatus for automatically removing well-strips from well-strip holders upon completion of the processing and/or pre-treatment of the wells. The apparatus includes a frame with an upper portion and a lower portion, the lower portion including a base plate with a plurality of cut-out sections each for receiving a well-strip holder.

The well-strip holders may be in the form of a molded plastic block having a base with a plurality of apertures extending completely therethrough. A well-receiving area is defined above each aperture by several posts extending upwardly from the base. The well-strips preferably are in the form of a sheet including a plurality of individual wells or cups connected together to form a single row or strip, e.g., twelve wells per strip. Adjacent groups of well-strips, e.g., four strips, may be held together at one end of the respective strips by, e.g., a common label(s). The well-strips are received in a well-strip holder with the individual wells or cups located above the apertures of the holder. The upper surface or portion of the well-strips, i.e., the flat portion located between adjacent wells or cups, preferably is flush with the upper surface of the well-strip holders. Preferably, the upper side of the base plate of the apparatus is coextensive with the well-strip holders.

The well-strip holders (with the well-strips positioned therein) are disposed in the cut-out sections of the base plate such that the well-strips are located on the underside of the base plate. That is, the well-strip holders preferably are inverted and positioned within the base plate such that the individual wells of the well-strips open downwardly. The apertures of the holders are open from above. A movable drive member is attached to the frame so as to be movable in a direction extending between the upper and lower frame portions, i.e., toward and away from the base plate.

A plurality of well-engaging portions, preferably corresponding to the number of well-strip holders, are fixed to the underside of the movable drive member. Each well-strip engaging portion includes a plurality of projections or pegs that may be moved downwardly into the apertures of a respective well-strip holder to engage the bottom of the inverted individual wells of the well-strips positioned therein. The projections contact the bottoms of the inverted wells and force the well-strips downwardly out of the holders and onto a conveyor for transporting the finished well-strips to a desired location.

BRIEF DESCRIPTION OF THE DRAWINGS

Other features, benefits and advantages of the present invention will be apparent from the following detailed description of a preferred embodiment thereof taken in conjunction with the accompanying drawing figures, wherein.

DETAILED DESCRIPTION OF THE DRAWINGS

Figure 1:
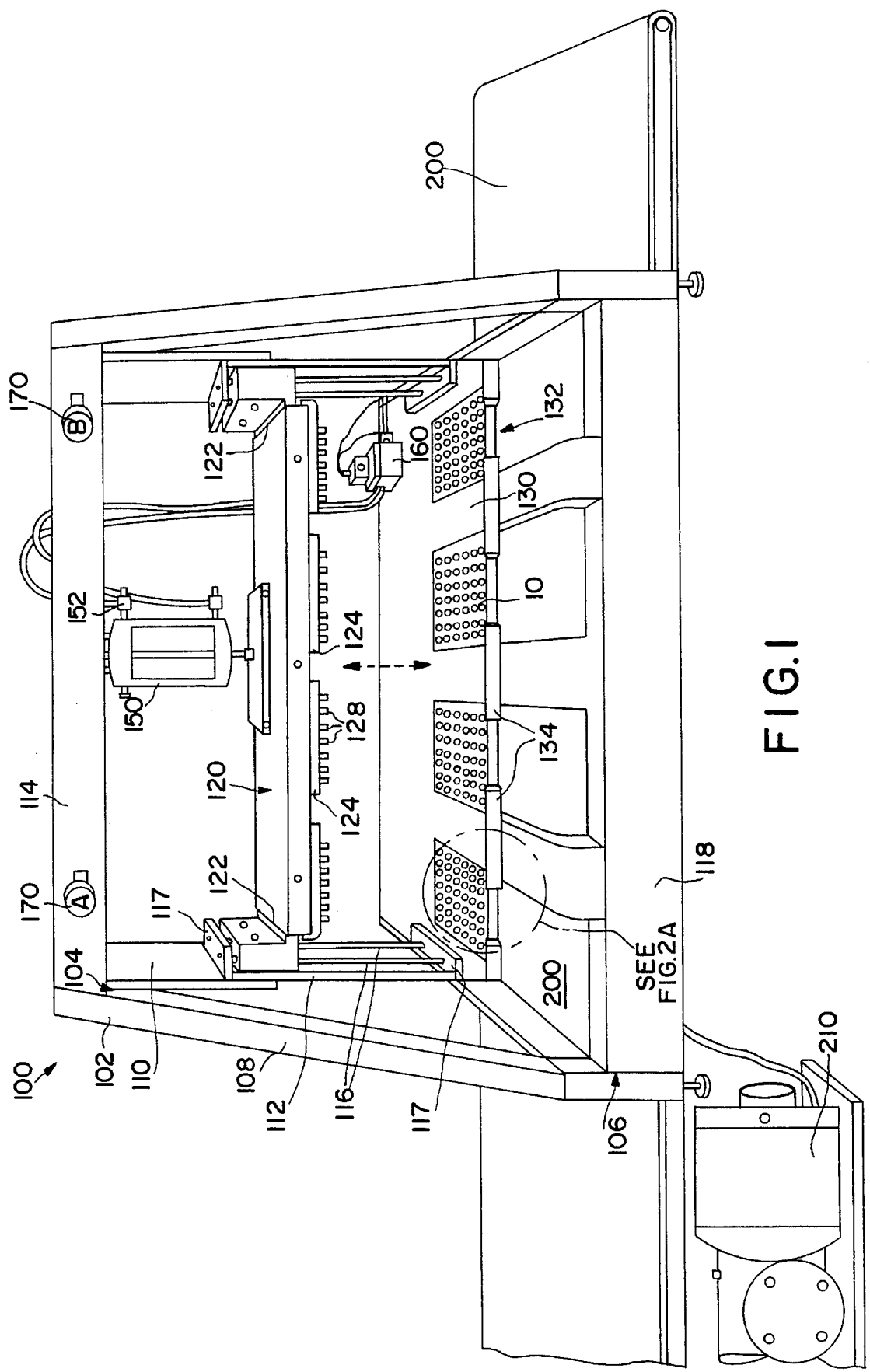
FIG. 1 is a perspective view of an apparatus for removing well-strips from well-strip holders according to the present invention.

With reference to FIG. 1, an apparatus for automatically removing microtiter well-strips from well-strip holders is indicated generally by the reference numeral 100 and includes a frame 102 and a base plate 130 with cut-out sections 132 for receiving well-strip holders 10. Well-strip holders 10 receive well-strips 30 (FIG. 2B) as mentioned above. The apparatus of the present invention may be used with numerous types of well-strips and well-strip holders, however, a preferred embodiment of same will be described with reference to FIGS. 2A–2C. The apparatus 100 will be described in detail below.

Figure 2A:
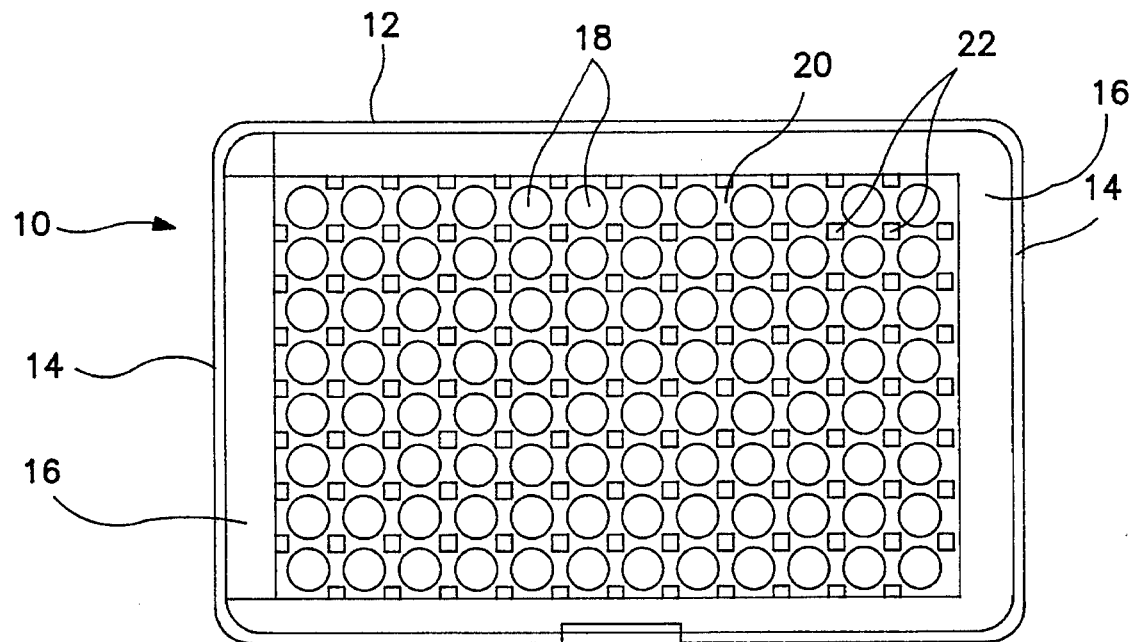
FIG. 2A is a plan view of a well-holder that may be used with the present invention.

FIG. 2A depicts a well-strip holder 10 which includes side portions 12, opposite ends 14, upper end portions 16, well apertures 18, base 20, posts 22, and well-receiving areas 24. The well-strip holder 10 preferably is formed of a rectangular block of plastic and may be molded, machined, etc. The block may be, e.g., ⅝" thick, 3¼" wide, and 5¼" long. FIG. 2C shows the well-strip holder 10 oriented so that the well-receiving areas or compartments 24 open upwardly. The areas 24 are defined by posts 22 which, as seen in FIG. 2A, are disposed in rows and columns. Between four adjacent posts 22 is a well aperture 18, which aperture passes through the base 20 of the well-strip holder (FIG. 2C). When the individual wells 32 of well-strip 30 are placed in the holder 10, each well 32 seats between four posts 22 (in an area 24) so as to overlie the well aperture 18. Thus, the bottom 36 of the wells can be contacted from beneath the well-strip holder 10 (as seen in FIG. 2C) via well apertures 18 formed in base 20.

Figure 2B:
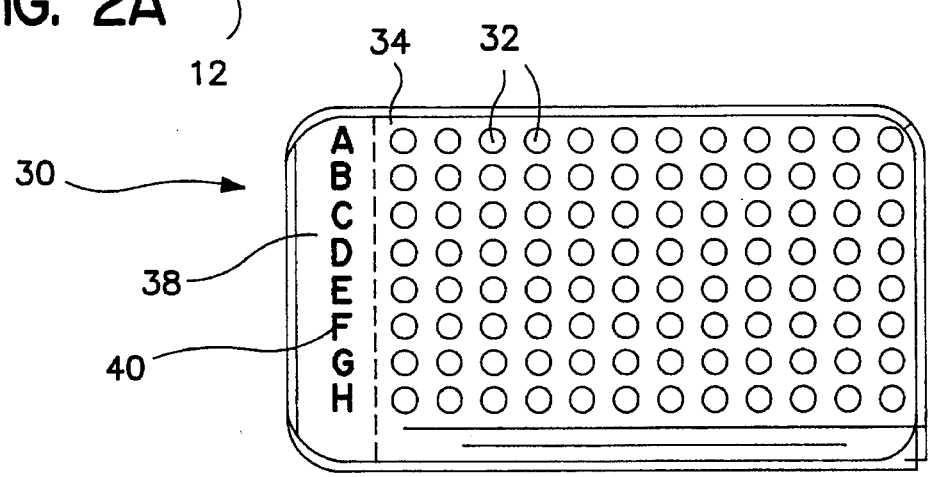
FIG. 2B is a plan view of a plurality of well-strips that may be used with the present invention.
Figure 2C:
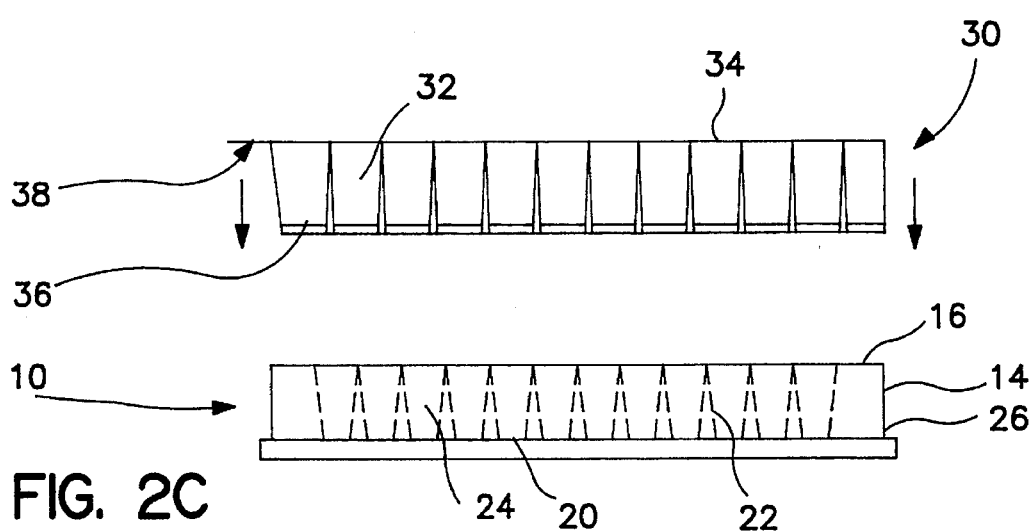
FIG. 2C is an exploded view of the complimentary well-strips and well-strip holder shown in FIGS. 2A and 2B.

Eight well-strips 30 with twelve wells 32 each are shown in FIG. 2B. The reference numeral 30 is used to refer to the plurality of well-strips which together form the 8×12 array of wells shown in FIG. 2B. The well-strips 30 may be connected in groups of four and joined by labels, e.g., one label per four strips and two labels per eight strips. It will, of course, be recognized that the specific number of wells and/or the configuration of the well-strips may vary. The well-strips 30 have a top 34, a bottom 36, individual wells 32, and an end panel 38. The end panel 38 of well-strip 30 preferably is received in a flush manner over upper end portion 16 of well-strip holder 10. The end portion 16 of well-strip holder 10 carries molded or machined alpha characters A–H 40, one letter corresponding to each row of well-strips 30. The well-strips 30 preferably are spaced slightly from the periphery of the holder 10.

Referring again to well-strip holder 10, it is seen that the base 20 thereof meets the opposite ends 14 and sides 12 so as to form a continuous step or flange 26. As will be explained below, this flange 26 engages the cut-out section 132 of base plate 130 of apparatus 100 to removably support the well-strip holder 10 thereon.

With attention direction to FIG. 1, the apparatus 100, constructed according to a preferred embodiment of the present invention, now will be described. Apparatus 100 includes a frame 102 which has an upper portion 104 and a lower portion 106 joined by upwardly extending front frame members 108 and vertical rear frame members (not shown in FIG. 1). Braces 110 are fixed to the upper portion 104 of frame 102 and extend downward with respect thereto. The lower end of each brace 110 is fixed to a support 112 which support has, at its upper and lower ends, transversely-directed plates 117. A pair of guide rods 116 is disposed between each set of plates 117, i.e., on opposite sides of apparatus 100. A movable drive member 120 is secured to the apparatus so as to be movable in a direction extending between upper and lower frame portions 104,106. The drive member 120 is movable toward and away from base plate 130 which supports the well-strip holders 10.

The ends of movable drive member 120 are provided with pillow blocks 122 having elongated bearing apertures extending therethrough. The blocks 122 are slidably received over guide rods 116 via said bearing apertures and support the drive member 120 as it moves linearly toward and away from the base plate 130. Movable drive member 120 is driven by an air cylinder 150 provided with a suitable speed control 152 for setting the speed at which member 120 will be driven. Air is fed to the air cylinder 150 via a solenoid valve 160, the operation of which will be readily understood by those skilled in the art.

Figure 4:
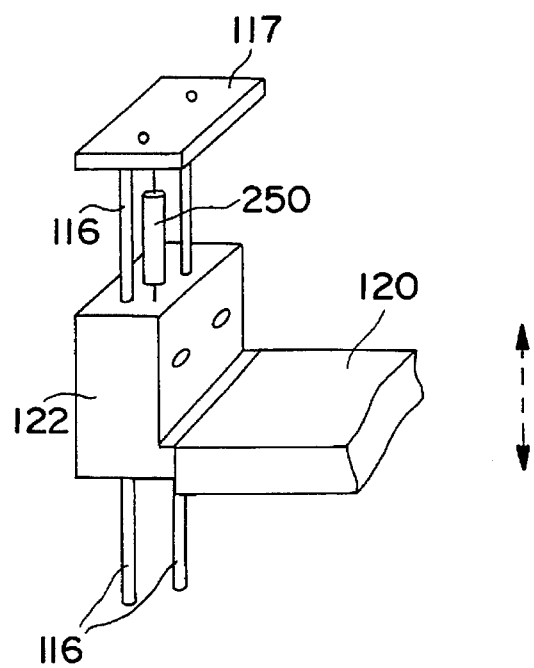
FIG. 4 is a perspective view of the apparatus shown in FIG. 1 modified according to another embodiment of the present invention.

In an alternative embodiment of the present invention shown in FIG. 4, the movable drive member 120 is driven by a pair of air cylinders 250, one cylinder being disposed at each of the opposite ends of movable member 120. FIG. 4 depicts only one end of member 120 which in this embodiment includes an air cylinder 250 (shown schematically) disposed between and fixed to the upper transverse plate 117 and pillow block 122. Air cylinders 250 are activated as described above with respect to air cylinder 150, whereby pillow block 122 and drive member 120 are selectively moved in the direction of the arrows. The opposite end of the apparatus (not shown in FIG. 4) also has an air cylinder 250 such that the two cylinders force the ends of movable drive member 120 in the desired direction. Of course, it will be readily recognized that various configurations of air cylinders or drive means may be utilized in the present invention.

Figure 5:
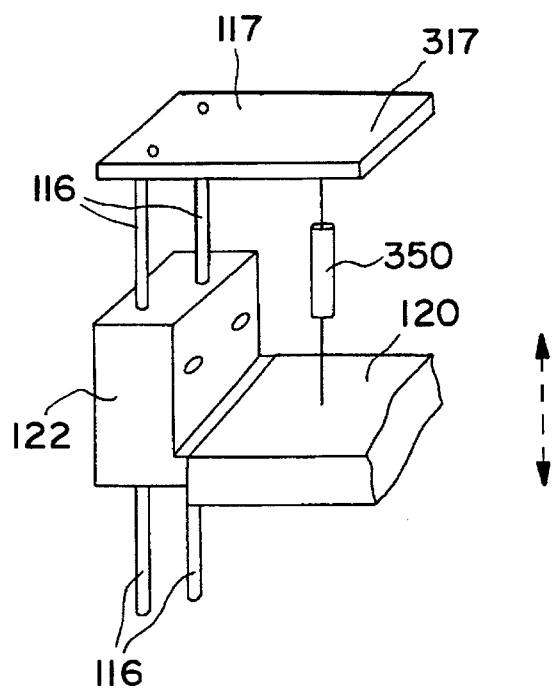
FIG. 5 is a perspective view of the apparatus shown in FIG. 1 modified according to yet another embodiment of the present invention.

In yet another embodiment of the present invention shown in FIG. 5, two air cylinders 350 are used to drive the movable member 120 by directly engaging the opposite ends of member 120. The cylinders 350 are positioned at and fixed to the opposite ends of movable member 120 and transversely-directed plates 117 so as to be spaced inwardly of pillow blocks 122. As seen in FIG. 5, the upper transverse plate 117 at each end of the apparatus has an extended portion 317 directed toward the center of the apparatus so as to overlie the movable member 120. This portion 317 provides a support to which a respective air cylinder 350 is fixed. As with FIG. 4, FIG. 5 shows only one end of the apparatus, with the opposite end thereof being configured in a similar fashion. The operation of the air cylinders 350 is as described above with respect to the previous embodiments.

Actuating switches 170 are used to actuate apparatus 100. In a preferred embodiment, a safety feature is provided in that it is necessary to depress both switches 170 in order to activate the apparatus. This prevents the user from inadvertently activating the machine while replacing the well-strip holders, servicing the equipment, etc. As seen in FIG. 1, the switches 170 may be in the form of palm switches located at opposite ends of frame cross member 114.

Movable drive member 120 has secured on its underside, i.e., opposite the air cylinder 150, at least one, and preferably a plurality of well-strip engaging portions 124. Although the number of portions 124 may be varied, it is desirable to have same correspond to the number of base plate cut-out sections 132 so that one portion 124 removes the well-strips from one well-strip holder. The well-strip engaging portions 124 each include a base 126 with a plurality of projections or pegs 128. The pegs 128 are aligned with the well apertures 18 of well-strip holders 10 as described below.

The operation of the apparatus 100 now will be described. The well-strip holders 10 typically are received at the apparatus 100 in the orientation shown in FIG. 2C after being pre-treated, except that the well-strips 30 are fully seated in well-strip holders 10. The well-strip holders 10 then are inverted and placed in the cut-out sections 132 of base plate 130. The well-strips 30 remain in holders 10 due to the relatively tight friction-fit therebetween.

Figure 3A:
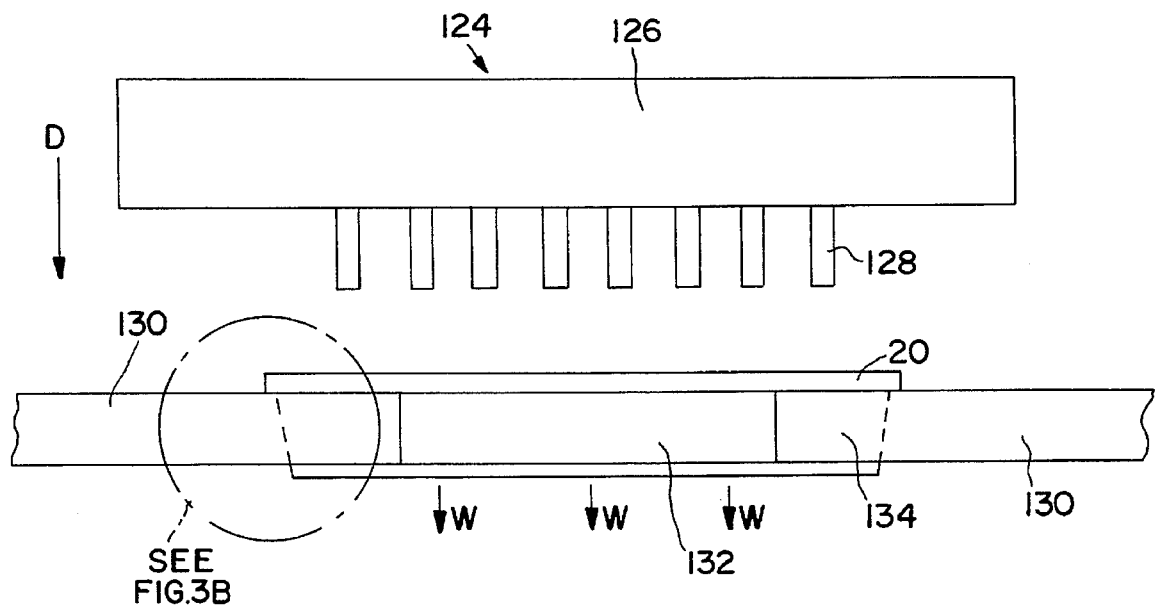
FIG. 3A is an enlarged view of the portion encircled by "A" in FIG. 1.
Figure 3B:
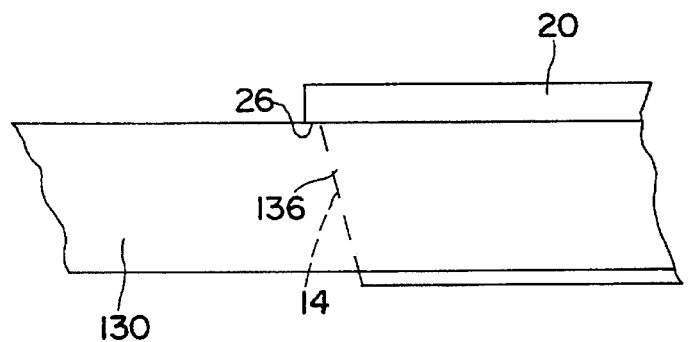
FIG. 3B is an enlarged view of the portion encircled by "B" FIG. 3A.

FIG. 3A shows a side view of well-strip holder 10 positioned in base plate 130. As seen in FIG. 1, cut-out sections 132 have a reduced-width front portion due to extended flanges 134. Flanges 134 and base plate 130 form a seat which receives the stepped continuous flange portion 20 of well-strip holder 10. See FIG. 3B. The stepped portion 20 rests on the upperside of base plate 130 with the well-strips 30 facing downward. A conveyor 200 is driven by a motor 210 and is disposed beneath apparatus 100 so as to be directly beneath the cut-out sections 132.

Upon actuation of the apparatus via switches 170, movable drive member 120 is driven toward base plate 130. FIG. 3A shows a well-strip engaging portion 124 with base 126 and projections or pegs 128. The arrow "D" indicates the movement of portion 124 toward base plate 130. The pegs 128 are aligned with the well apertures 18 of each inverted well-strip holder 10. When movable drive member 120 reaches the base plate 130, the pegs 128 enter the well apertures 18 of the holders 10 and contact the bottom 36 of some or all of the wells 32 to pop the well-strips 30 from the holders 10. Of course, the specific number and/or configuration of pegs 128 on bases 126 may be varied. A significant aspect of the present invention resides in providing a sufficient number of pegs to easily dislodge the well-strips from the holders upon downward movement of the movable drive member. After being forced out of the well-strip holders, the well-strips fall onto a conveyor 200 and are transported to a location for inspection, packaging, etc.

It is apparent that the present invention provides an apparatus for removing microtiter well-strips from holders therefore that is superior to prior art removal apparatus. The many benefits of the present invention include the ability to remove well-strips from several holders, e.g., four, at one time, as opposed to manually removing the strips from one holder at a time. The loading and unloading of well-strip holders in and from the apparatus is extremely easy and can be performed by relatively unskilled workers without damaging the optical surfaces of the wells. In addition, the present invention ensures precise alignment between the pegs of the well-strip engaging portions and the apertures in the well-strip holders to prevent damage to the holders.

Although the present invention has been described with reference to particular embodiments, it is to be understood that the embodiments are merely illustrative of the application of the principles of the invention. Numerous configurations may be made therewith without departing from the spirit and scope of the invention.

What is claimed is:

1. An apparatus for automatically removing microtiter well-strips from a plurality of well-strip holders, each well-strip holder having a base plate and including a plurality of well-receiving areas configured to receive an individual well of a well-strip and an aperture located beneath each of said well-receiving areas, the well-strip including a plurality of individual wells which are adapted to receive a sample of material to be tested, the apparatus comprising:

a frame having an upper portion and a lower portion;

a base plate secured to the lower portion of said frame, said base plate including a plurality of cut-out sections for removably supporting a plurality of well-strip holders;

a movable member mounted on said frame so as to be movable in a direction extending between the upper and lower portions of said frame and toward and away from said base plate;

a device for moving said movable member toward and away from said base plate;

wherein said movable member has secured thereto a plurality of well-strip engaging portions corresponding to the cut-out sections of the base plate, each well-strip engaging portion including a plurality of projections for being moved through the apertures of a respective well-strip holder to engage the individual wells of the well-strips and remove the well-strips from the well-strip holders.

2. An apparatus as claimed in claim 1, wherein the movable member is secured to a plurality of guide rods fixed to the frame so as to be movable linearly toward and away from said base plate.

3. An apparatus according to claim 1, wherein said device for driving the movable member includes at least one air cylinder fixed to the frame and to the movable member so that when actuated, the air cylinder drives the movable member toward or away from said base plate.

4. An apparatus according to claim 3, wherein a solenoid valve controls the passage of air to the air cylinder and is operable by an actuating button.

5. An apparatus according to claim 4, wherein the solenoid valve is operable by two actuating buttons, and both said buttons must be actuated to activate the solenoid valve and feed air to the air cylinder.

6. An apparatus according to claim 3, wherein the air cylinder has a control device for setting the cylinder to a desired operating speed at which the movable member is moved toward and away from said base plate.

7. An apparatus according to claim 3, wherein two air cylinders respectively are fixed to the frame and to two opposite ends of the movable member to drive the movable member toward or away from said base plate.

8. An apparatus for automatically removing microtiter well-strips from at least one well-strip holder, the well-strip holder including a base and a plurality of well-receiving areas overlying the base for receiving a plurality of individual wells of at least one well-strip, and an aperture extending through the base beneath each well-receiving area, the plurality of wells of said well-strip being configured to receive a sample of a material to be tested, the apparatus comprising:

a frame having an upper portion and a lower portion;

a base plate secured to the lower portion of said frame, said base plate including at least one cut-out section for removably supporting the at least one well-strip holder;

a movable member mounted on said frame so as to be movable in a reciprocating manner between the upper and lower portions of said frame toward and away from said base plate;

a device for driving said movable member toward and away from said base plate;

wherein said movable member has secured thereto at least one well-strip engaging portion which includes a plurality of pegs aligned with the apertures in the base of the at least one well-strip holder and being selectively movable into the apertures thereof to engage the wells of the well-strip and remove the well-strip from the well-strip holder.

9. An apparatus according to claim 8, wherein the movable member is secured to a plurality of guide rods fixed to the frame so as to be movable linearly toward and away from said base plate.

10. An apparatus according to claim 9, wherein a pillow block is secured to each of two opposite ends of the movable member with the plurality of guide rods received in elongated bearing openings formed in each pillow block.

11. An apparatus according to claim 8, wherein the movable member has a top and bottom surface, and the at least one well-strip engaging portion is secured to the bottom surface for engaging the apertures in the at least one well-strip holder when the movable member is moved toward said base plate.

12. An apparatus according to claim 11, wherein the base plate has four cut-out sections for receiving four well-strip holders, and the movable member has four well-strip engaging portions which are aligned with the respective well-strip holders when said holders are disposed in the cut-out sections, each of said well-strip engaging portions having a plurality of pegs that are movable into the apertures of a respective well-strip holder to remove the well-strips therefrom.

13. An apparatus according to claim 11, wherein said base plate is configured such that the cut-out sections receive the well-strip holder with the well-strip located on an underside of the holder, and the movable member forces the well-strip downwardly away from the well-strip holder.

14. An apparatus according to claim 13, wherein a conveyor is disposed beneath the base plate and receives the well-strip upon its removal from the well-strip holder.

15. An apparatus according to claim 8, wherein said device for driving the movable member includes at least one air cylinder fixed to the frame and to the movable member so that when actuated, the air cylinder drives the movable member toward or away from said base plate.

16. An apparatus according to claim 15, wherein a solenoid valve controls the passage of air to the air cylinder and is operable by an actuating button.

17. An apparatus according to claim 16, wherein the solenoid valve is operable by two actuating buttons, and both said buttons must be actuated to activate the solenoid valve and feed air to the air cylinder.

18. An apparatus according to claim 15, wherein the at least one air cylinder has a control device for setting the cylinder to a desired operating speed at which the movable drive member is moved toward and away from said base plate.

19. An apparatus according to claim 15, wherein two air cylinders respectively are fixed to the frame and to two opposite ends of the movable member to drive the movable member toward or away from said base plate.

* * * * *